United States Patent [19]
Elgavish et al.

[11] Patent Number: 6,032,069
[45] Date of Patent: Feb. 29, 2000

[54] PHYSIOLOGICAL TRIGGERING DEVICE FOR HIGH-FIELD MAGNETIC-RESONANCE INSTRUMENTATION

[75] Inventors: Gabriel A. Elgavish, Hoover; Rotem L. A. Elgavish; Tamas Simor, both of Birmingham, all of Ala.

[73] Assignee: Uab Research Foundation, Birmingham, Ala.

[21] Appl. No.: 09/071,308

[22] Filed: May 1, 1998

[51] Int. Cl.[7] .................................................. A61B 5/055
[52] U.S. Cl. ........................................ 600/413; 600/521
[58] Field of Search .................................. 600/413, 428, 600/508, 509, 521

[56] References Cited

U.S. PATENT DOCUMENTS

| | | |
|---|---|---|
| 4,694,837 | 9/1987 | Blakeley et al. . |
| 4,712,560 | 12/1987 | Schaefer et al. . |
| 4,736,328 | 4/1988 | Vatis et al. ............................... 364/484 |
| 4,752,734 | 6/1988 | Wedeen .................... 324/306 |
| 4,777,957 | 10/1988 | Wehrli et al. . |
| 4,800,889 | 1/1989 | Dummoulin et al. . |
| 4,855,910 | 8/1989 | Bohning . |
| 4,903,704 | 2/1990 | Van Eggermond et al. ........... 600/413 |
| 4,979,512 | 12/1990 | Heubes . |
| 4,995,394 | 2/1991 | Cline et al. . |
| 5,000,182 | 3/1991 | Hinks . |
| 5,245,288 | 9/1993 | Leussler .................... 324/322 |
| 5,251,628 | 10/1993 | Foo . |
| 5,317,260 | 5/1994 | Kasten et al. ........................... 324/309 |
| 5,352,979 | 10/1994 | Conturo .................. 324/307 |
| 5,429,134 | 7/1995 | Foo . |
| 5,474,067 | 12/1995 | Laub . |
| 5,517,117 | 5/1996 | Mueller et al. .......................... 324/306 |
| 5,530,356 | 6/1996 | Yokoi ....................... 324/318 |
| 5,545,992 | 8/1996 | Foo ........................ 324/309 |
| 5,611,341 | 3/1997 | Aritomi et al. . |

FOREIGN PATENT DOCUMENTS

| | | |
|---|---|---|
| 0 205 136 A2 | 12/1986 | European Pat. Off. . |
| 0 285 862 B1 | 10/1988 | European Pat. Off. . |
| 0 412 695 A2 | 2/1991 | European Pat. Off. . |

*Primary Examiner*—Ruth S. Smith
*Attorney, Agent, or Firm*—Gifford, Krass, Groh, Sprinkle, Anderson & Citkowski, P.C.

[57] ABSTRACT

Refractory delay circuitry ensures that induced currents do not falsely rigger the acquisition phase of magnetic-resonance instrumentation. Immediately after the triggering of the acquisition sequence, for example, by the R-wave of a subject's cardiac cycle, the adjustable delay circuit is used to inhibit further trigger signals for a predetermined duration of the acquisition gradient activity. The acquisition sequence will thus not be triggered by extra peaks in the biological signal, which may take the form of non-R-wave signals in the cardiac cycle. In this embodiment of the invention triggering will occur only at most once per heartbeat. As cardiac signals may be divided into two major groups, electrical (ECG) and non-electrical (e.g., coronary artery pressure wave, or arterial flow signals) which exhibit two different frequency ranges, the invention typically utilizes separate filtering components for the isolation of these two types of signals, thus allowing for the selection of either stimulus for triggering purposes.

9 Claims, 4 Drawing Sheets

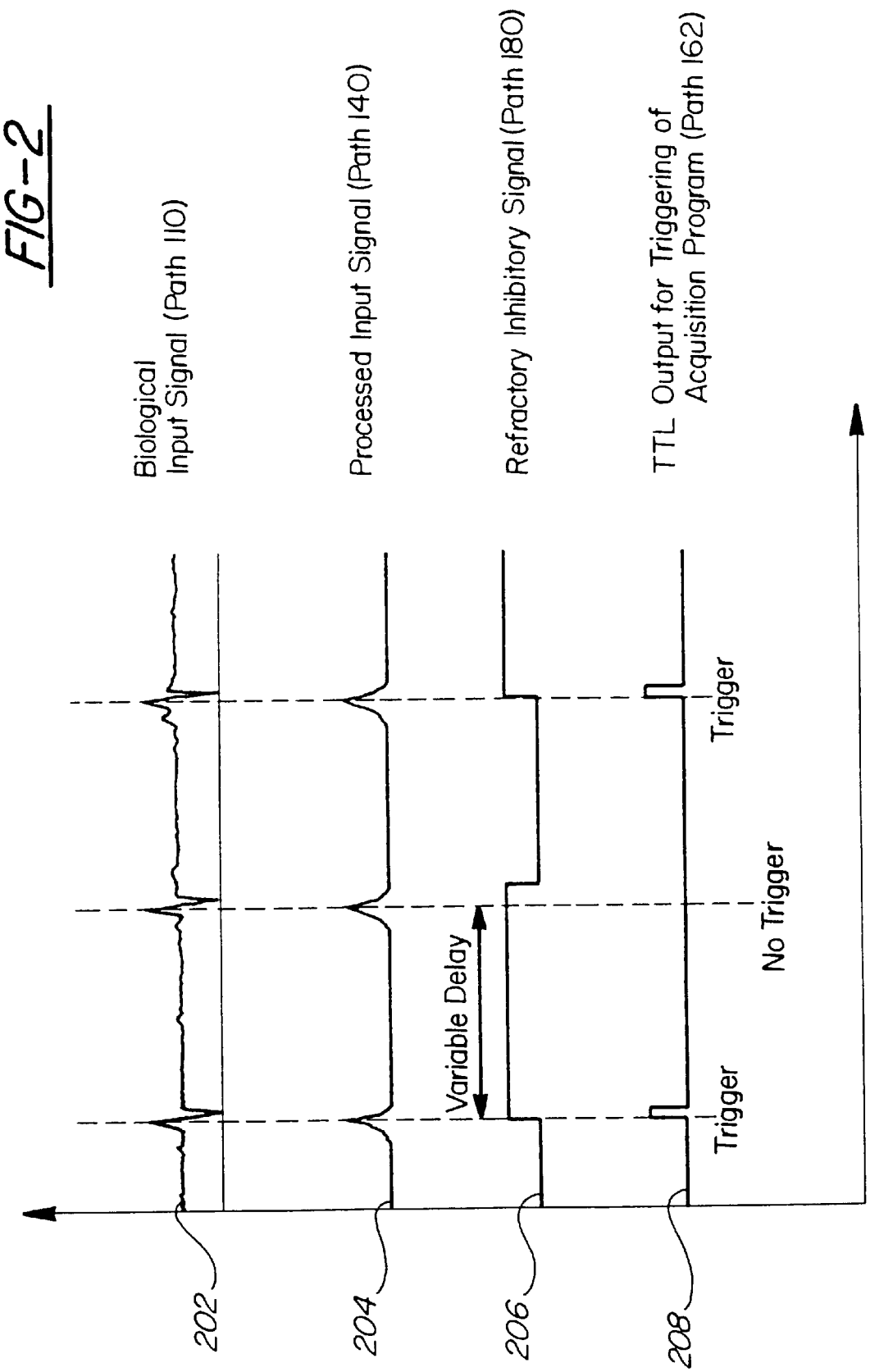

6,032,069

PHYSIOLOGICAL TRIGGERING DEVICE FOR HIGH-FIELD MAGNETIC-RESONANCE INSTRUMENTATION

FIELD OF THE INVENTION

The present invention relates generally to nuclear magnetic resonance and, in particular, to a physiological triggering device for high-field MRI/NMR instruments using a refractory delay to prevent interference from gradient currents.

BACKGROUND OF THE INVENTION

Magnetic resonance imaging is increasingly being used by physicians for diagnostic purposes. In the last several years, in particular, cardiac magnetic resonance imaging (MRI) and MRS have become increasingly capable in terms of functionality, yet affordable due to hardware and software improvements, particularly those associated with image acquisition.

In order to acquire a clear cardiac image without motion artifacts, however, the activation of the acquisition sequence must be precisely correlated with the beginning of each cardiac cycle. Although cardiac triggering devices currently exist in the field of nuclear magnetic resonance, such devices suffer from currents which are induced by the dynamic field resulting from gradients used in the acquisition phase. As there is a trend toward higher magnetic fields, and stronger gradients, this problem of induced currents is worsening, and must, therefore, be addressed.

SUMMARY OF THE INVENTION

Broadly, the present invention addresses the problem of induced currents in a physiological trigger through the use of a timing circuit to produce a refractory delay. Immediately after the triggering of the acquisition sequence, for example, by the R-wave of a subject's cardiac cycle, an adjustable timing circuit is used to inhibit further trigger signals for a predetermined duration of the acquisition gradient activity. During this refractory delay period, any stray currents induced by the gradients of the acquisition sequence will not trigger a false sequence. In particular, the acquisition sequence will not be triggered by extra peaks in the biological signal, which may take the form of non-R-wave signals in the cardiac cycle. In this embodiment of the invention, triggering will occur only at most once per heartbeat.

The length of the refractory period may be adjusted, as needed, through the circuitry according to the invention. Since cardiac signals may be divided into two major groups, electrical (EKG) and non-electrical (e.g., coronary artery-pressure waves, arterial flow signals), which exhibit two different frequency ranges, the invention typically utilizes separate filtering components for the isolation of these two types of signals, thus allowing for the selection of either type of stimulus for triggering purposes.

BRIEF DESCRIPTION OF THE DRAWINGS

FIG. 2 is a representative timing diagram of important signals related to the invention.

DETAILED DESCRIPTION OF THE INVENTION

The present invention is directed toward a triggering device for use with nuclear magnetic resonance (NMR) and magnetic-resonance imaging (MRI), which utilizes a refractory delay to prevent unwanted trigger signals. That is, whenever physiological gating is required while using a high-field magnetic-resonance instrument, the invention serves to prevent unwanted triggering of the acquisition sequence, resulting in superior imaging. Although in the preferred embodiment and the following description a cardiac-based signal is used as a primary trigger, it will be evident to one of skill that other physiological stimuli may be also used as a primary input(s).

The physiological signal is acquired through leads attached to the subject (not shown). In a preferred embodiment, ECG leads are attached to the subject, and the physiological signal is acquired through an ECG telemetric system (e.g., one manufactured by the Hewlett-Packard Company). The received signal is then routed to a universal interface module (the UIM100) produced by BIOPAC Systems, Inc. This universal interface module includes a number of analog and digital connectors, and the circuitry depicted and described herein interconnects to certain pins of this connector, enabling a straightforward coupling and decoupling of the instrumentation. In particular, the analog cardiac signal typically used for triggering is sent to channel 8 of the UIM100, which enters the circuitry depicted in FIG. 1A through pin 27. In operation, the refractory period is then set to the desired length of time, and the inventive circuitry, best understood with reference to FIG. 1C, generates a TTL-level output to trigger the acquisition program of an appropriate NMR spectrometer/imager of commercial design. With particular reference to the UIM100, the trigger signal is delivered to channel 16 of the interface, and, from there, is delivered to the spectrometer.

Figure 1A:
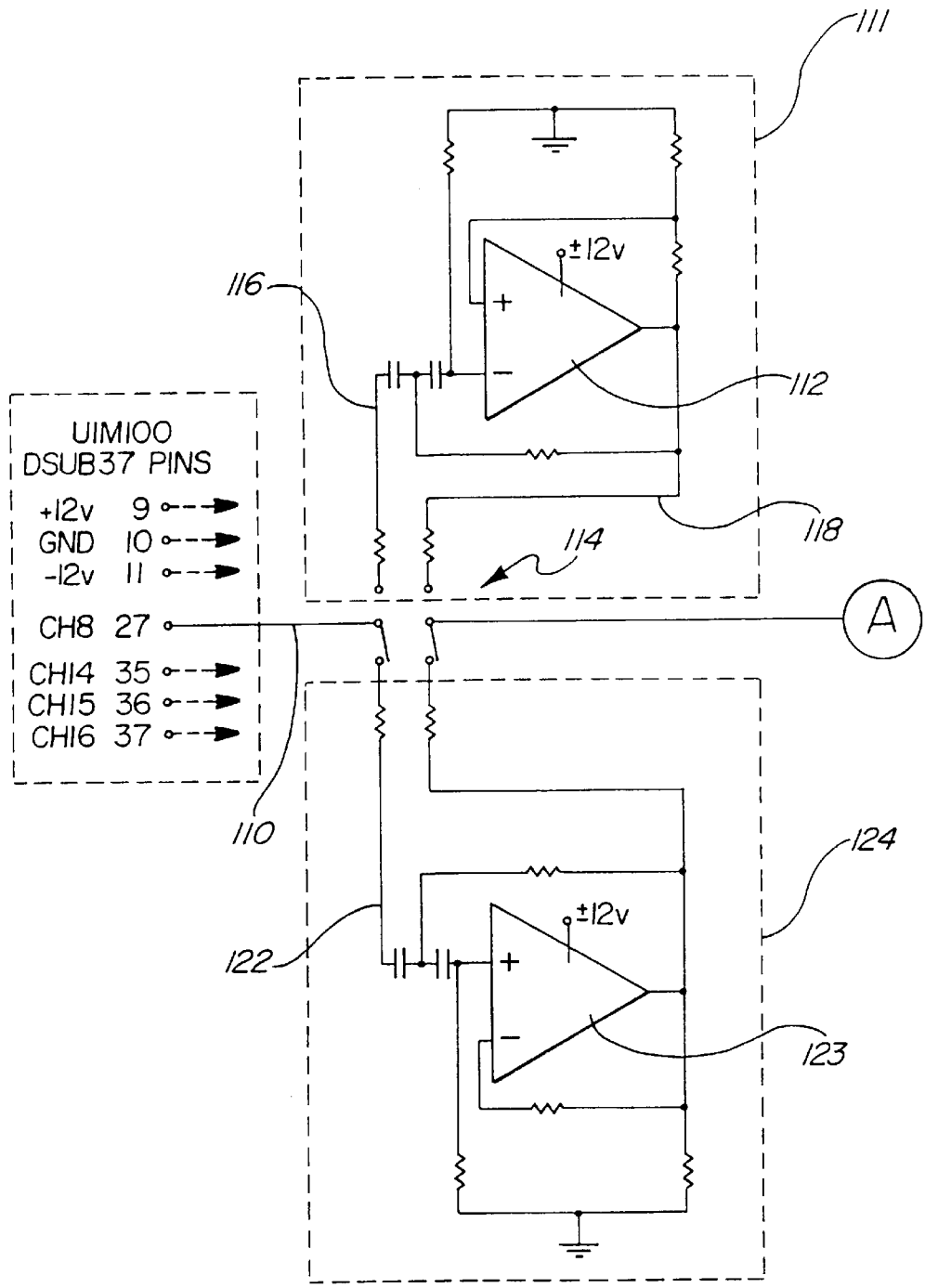
FIG. 1A illustrates, in block diagram form, electrical circuitry associated with the input filtering of a cardiac trigger device for MRI/NMR applications.

Now making reference to the drawings, FIG. 1A illustrates, in block-diagram form, input circuits associated with a cardiac triggering device according to the invention. The acquired physiological signal enters the device by way of path 110, having been routed through channel 8, pin 27 of the UIM100 as discussed above. Low-frequency signals are first filtered out using a high-pass filter arrangement. For ECG signals, a 16-Hz high-pass 111 filter is used to filter out all but the main QRS peak, which is then used for triggering purposes. A separate, 2-Hz high-pass filter 124 is used in conjunction with pressure-wave inputs, with a double-pole, double-throw switch 114 being used for selective routing of the input signal.

Figure 1B:
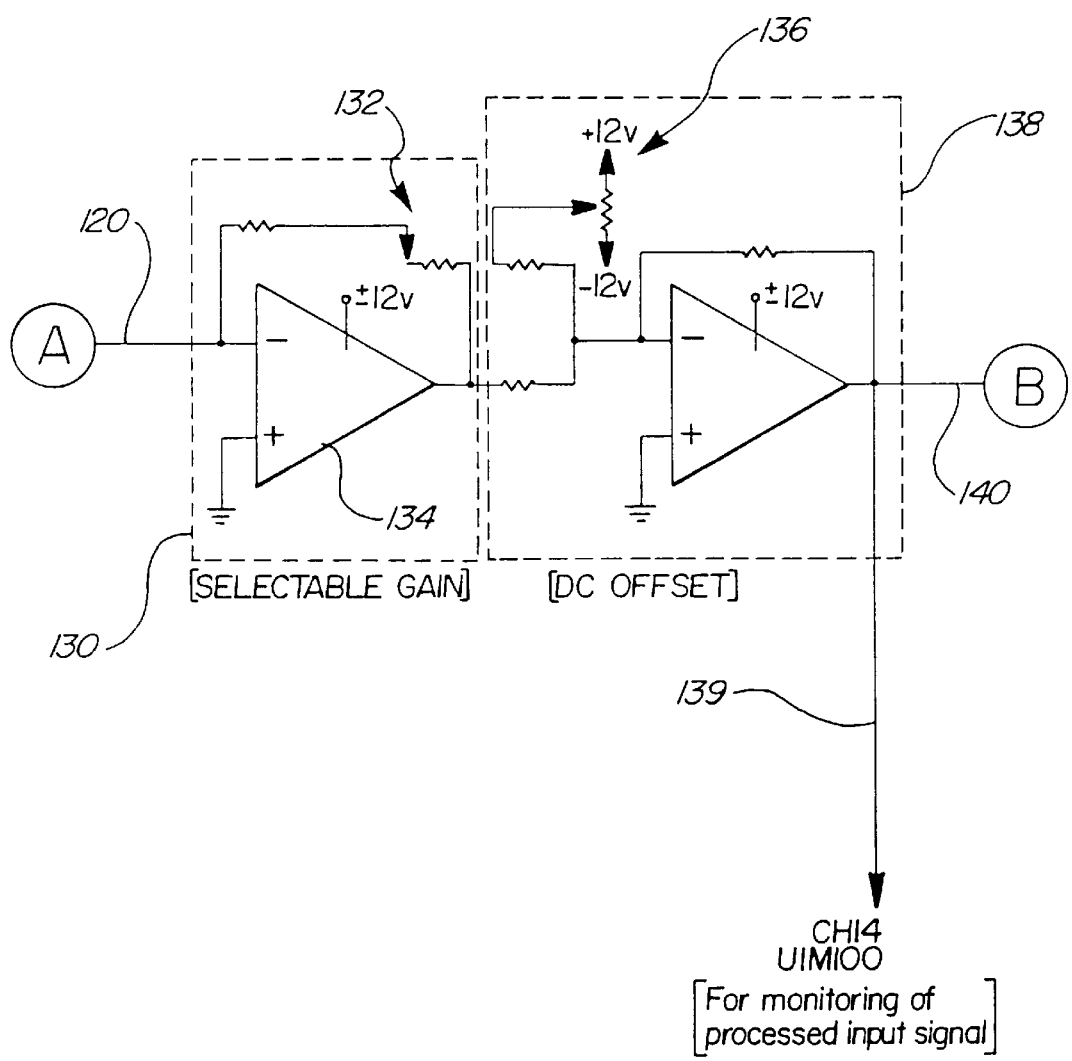
FIG. 1B illustrates, in block-diagram form, selectable gain and DC-offset circuits.

With switch 114 in an upward orientation (not shown in the figure), the signal along path 110 is directed into the ECG filter 111 along path 116, and output by the filter along path 118, to path 120, which is reproduced in FIG. 1B. With switch 114 in the downward position (as shown in the figure), the signal along path 110 is directed to path 122 into the 2-Hz high-pass filter 124 for pressure-wave inputs. Both filters are conveniently based upon respective commercially available operational amplifiers 112 and 123 such as the LM741, with appropriate feedback components to provide the desired high-pass response.

Figure 1C:
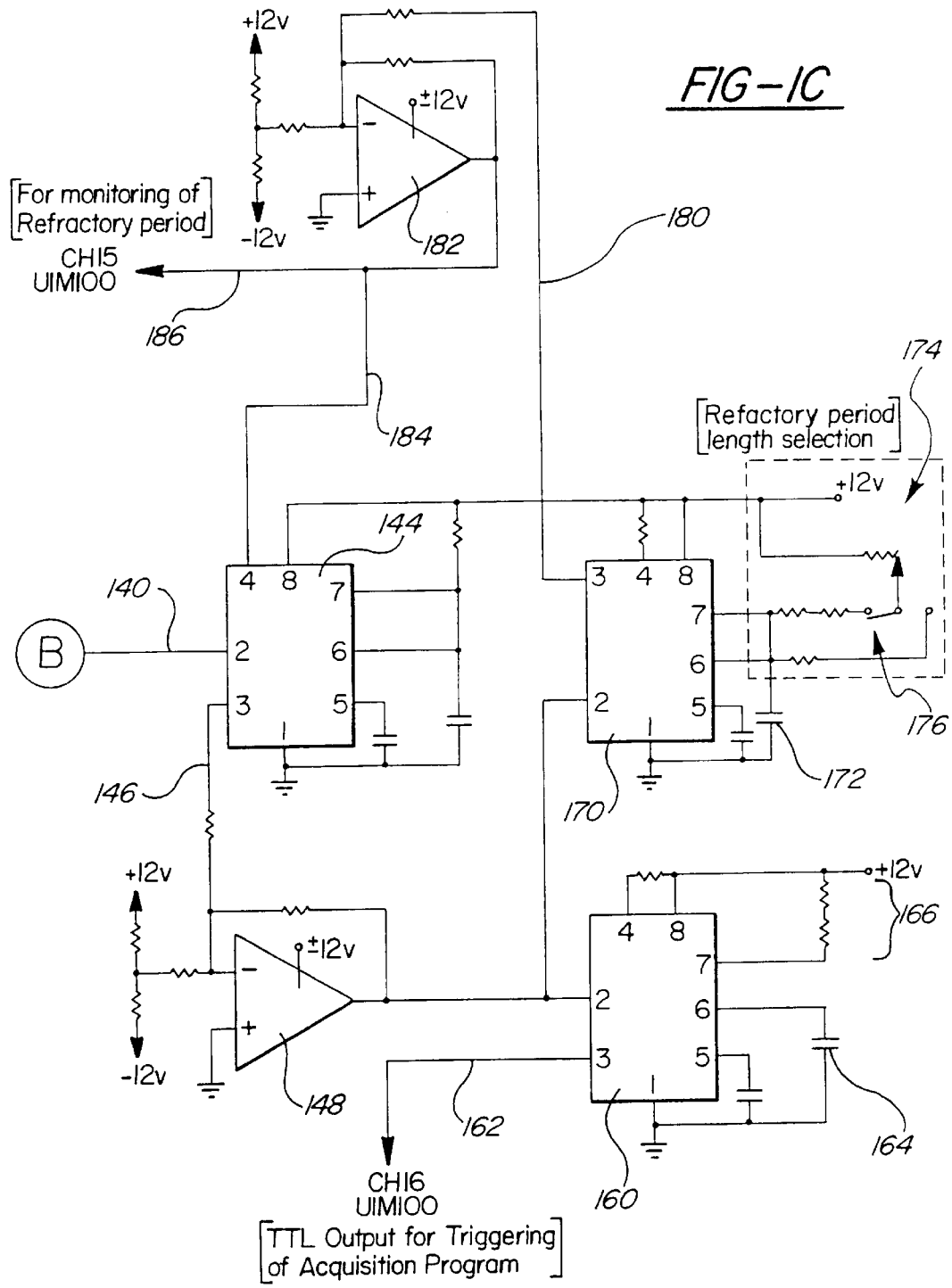
FIG. 1C illustrates, also in block-diagram form, timing circuits operative to generate a refractory delay according to the invention.

Now turning to FIG. 1B, the signal present along path 120, whether from filter 111 or filter 124, is presented to a selectable-gain circuit 130 which, in turn, feeds a DC offset circuit 138, outputting a gain- and DC-adjusted signal along path 140, which is reproduced in FIG. 1C. Path 139 may optionally be provided as an output for the purposes of monitoring the processed input signal along path 140 for interconnection, for example to channel 14 of the UIM100 interface.

The selectable gain circuit 130 uses a potentiometer 132 to vary the degree of amplification provided by operational amplifier 134, through placement of the variable resistance in a feedback path to the inverting input of the OP AMP 134. Having adjusted for gain, a second potentiometer 136 associated with DC offset circuit 138 may be used to bring the analog signal back to baseline to ensure proper triggering of a first monostable timer 144, depicted in FIG. 1C. Referring to FIG. 1C, the device 144, having been triggered along path 140 (input 2), outputs a signal along path 146, through amplifier 148, to trigger second and third monostable timers 160 and 170, respectively. As with timer 144, these additional timers may be implemented using a commercially available unit such as the 555 device available from various manufacturers.

The device 160 outputs a TTL-level signal along path 162, which is used for the triggering of the acquisition phase, with the timing of the trigger being determined by capacitor 164 and resistors 166. Monostable device 170, on the other hand, is used to determine the length of the refractory delay period, in conjunction with capacitor 172 and a resistance 174, which is adjustable to bring about a variable delay. For a wider range of variability, a switch 176 may be used to place different resistances in series with the potentiometer 174, as shown.

The output of timer 170, along path 180, feeds an amplifier 182, the output of which is delivered along path 184 to the inhibit input (pin 4) of the device 144, thereby establishing the refractory period. More particularly, the third timer 170 assures that the first timer 144 cannot be retriggered until the refractory period terminates, thereby preventing any unwanted triggering of the acquisition program by induced currents or voltage spikes. A monitoring of the refractory period may optionally be delivered along path 186, utilizing one of the pins of the UIM100 connector.

FIG. 2 is a diagram which shows the relationship among various electrical signals according to the invention. Reference is made to path numbers in FIGS. 1A to 1C. Signal 202 illustrates a biological input signal, in particular, the R-wave of a patient's cardiac cycle. This signal is processed to produce a waveform 204 having peaks strongly correlated to the R-peaks. As shown in waveform 206, a refractory inhibiting signal is generated, having an onset coincident with the first R-peak shown in the figure, and a variable delay in accordance with the circuitry described above. Waveform 208 illustrates the TTL output for triggering of the acquisition program along path 162. Note that, with the variable delay extended past the second R-peak shown in the figure, TTL-level triggers occur only for every other biological input signal, thereby preventing false triggers.

We claim:

1. An electronic triger for use with a high-field magnetic-resonance instrument having an acquisition-phase, comprising:

an input for receiving a periodic physiological signal from a subject;

a pulse generator responsive to the physiological signal received from the subject for outputting an acquisition-phase triggering signal to the magnetic-resonance instrument; and variable-delay timer circuitry operative to inhibit the pulse generator during a refractory period following the output of the acquisition-phase triggering signal wherein the refractory period is at least one period of the periodic physiological signal.

2. The trigger of claim 1, wherein the periodic physiological signal from the subject is a cardiac signal.

3. The trigger of claim 1, further including a high-pass filter disposed in an electrical path between the input for receiving the periodic physiological signal and the pulse generator.

4. The trigger of claim 3, wherein the high-pass filter is a 16-Hz ECG filter.

5. The trigger of claim 3, wherein the high-pass filter is a 2-Hz pressure-wave filter.

6. The trigger of claim 1, wherein the pulse generator and variable-delay timer circuitry further comprise a first monostable multivibrator operative to generate the acquisition-phase triggering signal, and a second monostable multivibrator operative to generate the inhibit signal.

7. A method of triggering the acquisition phase of a high-field magnetic-resonance instrument, comprising the steps of:

receving periodic physiological signal from a subject;

generating the acquisition-phase triggering signal in response to the periodic physiological signal;

inhibiting the generation of any further acquisition-phase triggering signals during a refractory delay period; and triggering a pulse generator after at least two periods of the periodic physiological signal, wherein a refractory delay period between sequential triggerings at the pulse generator is at lease one periodic physiological signal.

8. The method of claim 7, wherein the step of receiving a periodic physiological signal from a subject includes receiving a cardiac-based signal.

9. A cardiac-based trigger for use with a high-field magnetic-resonance instrument having an acquisition-phase, comprising:

an input for receiving a cardiac signal from a subject characterized as a sequence of spaced-apart R-wave peaks;

a pulse generator operative to output an acquisition-phase triggering signal to the magnetic-resonance instrument in accordance with each R-wave peak; and variable-delay timer circuitry operative to inhibit the pulse generator during a refractory period between R-wave peaks to ensure that non-R-wave signals do not cause a false acquisition-phase triggering of the magnetic-resonance instrument wherein the refractory period is at least one period of the cardiac signal and independent of non-cardiac signal input.

* * * * *